United States Patent
Khanifar et al.

(10) Patent No.: US 9,949,321 B1
(45) Date of Patent: Apr. 17, 2018

(54) RADIO FREQUENCY FLUID WARMER

(71) Applicant: LINAMP TECHNOLOGIES LLC, Laguna Hills, CA (US)

(72) Inventors: Ahmad Khanifar, Laguna Hills, CA (US); Elham Khanifar, Laguna Hills, CA (US)

(73) Assignee: LinAmp Technologies LLC, Laguna Hills, CA (US)

( * ) Notice: Subject to any disclaimer, the term of this patent is extended or adjusted under 35 U.S.C. 154(b) by 0 days.

(21) Appl. No.: 15/454,051

(22) Filed: Mar. 9, 2017

Related U.S. Application Data

(60) Provisional application No. 62/305,998, filed on Mar. 9, 2016.

(51) Int. Cl.
| | |
|---|---|
| *H05B 6/80* | (2006.01) |
| *H05B 6/72* | (2006.01) |
| *A61B 17/30* | (2006.01) |
| *A61M 5/44* | (2006.01) |
| *A61M 1/28* | (2006.01) |

(52) U.S. Cl.
CPC ............... *H05B 6/802* (2013.01); *A61M 1/28* (2013.01); *A61M 5/445* (2013.01); *A61M 2205/3368* (2013.01); *A61M 2205/368* (2013.01)

(58) Field of Classification Search
CPC ..................... A61M 5/44; A61M 1/369; A61M 2205/3686; H05B 6/806
USPC .......... 604/27, 48, 14, 113, 114; 606/27–31; 607/90, 98–106
See application file for complete search history.

(56) References Cited

U.S. PATENT DOCUMENTS

| | | | | |
|---|---|---|---|---|
| 4,207,452 | A * | 6/1980 | Arai .................... | H05B 6/802 |
| | | | | 219/687 |
| 5,073,167 | A | 12/1991 | Carr et al. | |
| 5,683,381 | A | 11/1997 | Carr et al. | |
| 5,690,614 | A | 11/1997 | Carr et al. | |
| 5,895,548 | A * | 4/1999 | Ettinger ............ | H01J 37/32357 |
| | | | | 118/723 ME |
| 5,919,218 | A | 7/1999 | Carr | |
| 6,146,359 | A | 11/2000 | Carr et al. | |
| 2008/0277389 | A1* | 11/2008 | Carr .................... | A61M 5/44 |
| | | | | 219/761 |

* cited by examiner

*Primary Examiner* — Quang Van
(74) *Attorney, Agent, or Firm* — Jafari Law Group, Inc.

(57) ABSTRACT

The present invention is generally a radio frequency apparatus for warming fluids such as IV fluids. In exemplary embodiments, a uniform warming of fluids is achieved by exposing a fluid-carrying tube to Radio Frequency (RF) energy. The RF energy may be supplied by an RF generator, which is coupled to a waveguide. The waveguide typically includes an inlet into which a fluid tube may be introduced. Inside the waveguide, a pathway may be formed wherein the fluid tube may rest in a predetermined position. In exemplary embodiments, the pathway guides the positioning of the tube along a transmission-line length of the waveguide, in a manner such that the tube gradually approaches an electromagnetic field inside the waveguide and exits at a second terminal end of the waveguide. Having absorbed energy supplied from the RF generator, the fluid inside the tube exits the apparatus warmed to a desired temperature.

18 Claims, 11 Drawing Sheets

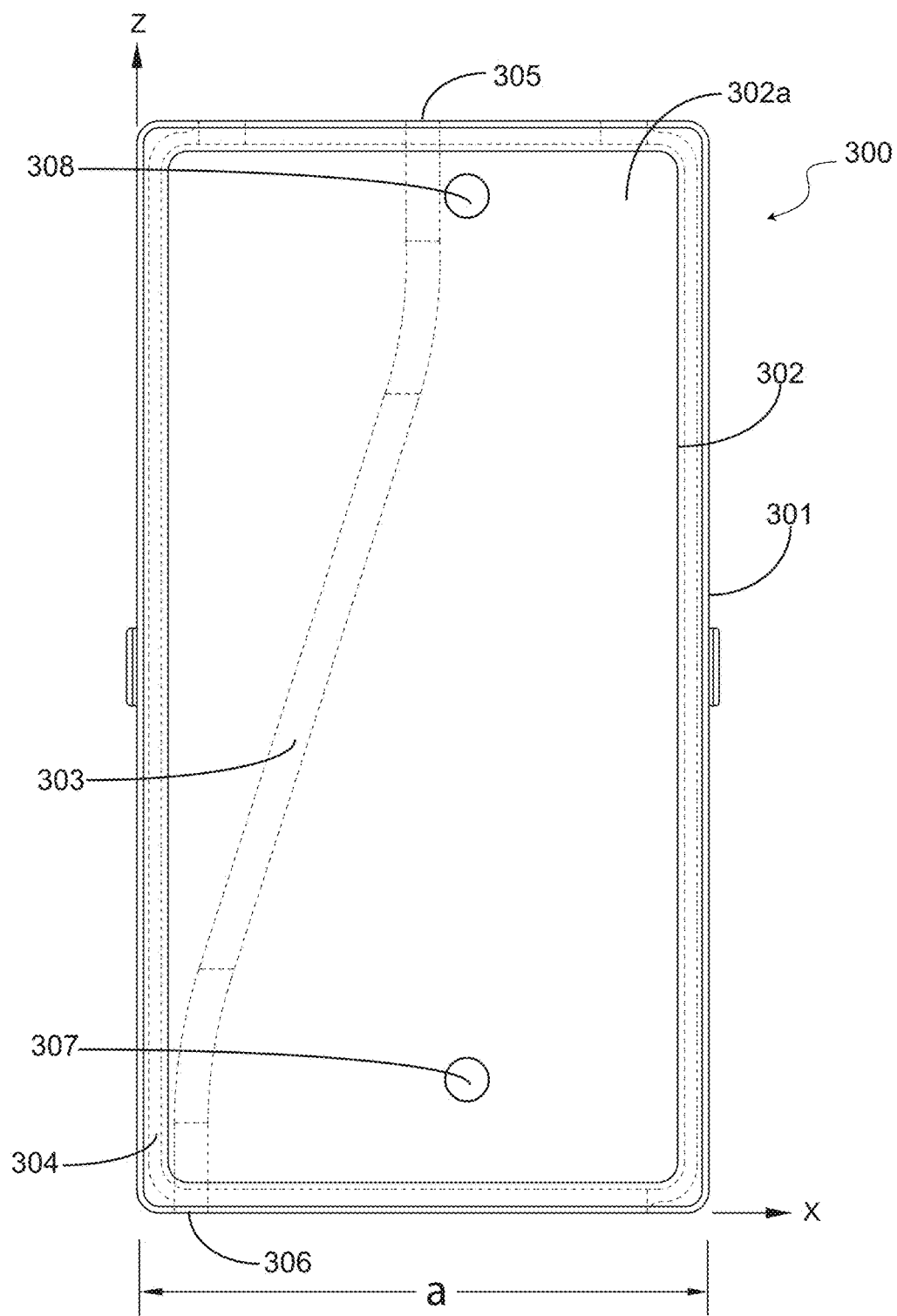

RADIO FREQUENCY FLUID WARMER

PRIORITY NOTICE

The present application claims priority under 35 U.S.C. § 119(e) to U.S. Provisional Patent Application Ser. No. 62/305,998 filed on Mar. 9, 2016, the disclosure of which is incorporated herein by reference in its entirety.

TECHNICAL FIELD OF THE INVENTION

The present invention relates in general to a system and method for warming fluids using radio frequency, and more specifically, to a radio frequency fluid warmer and method that may be utilized to warm therapeutic fluids.

COPYRIGHT & TRADEMARK NOTICE

A portion of the disclosure of this patent application may contain material that is subject to copyright protection. The owner has no objection to the facsimile reproduction by any one of the patent documents or the patent disclosures, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and shall not be construed as descriptive or to limit the scope of this invention to material associated only with such marks.

BACKGROUND OF THE INVENTION

Warming of fluids has various applications in any number of fields, for example medicine. In the medical field, warming of fluids is desirable during various procedures, particularly in those involving the intravenous administration of fluids to a patient. This issue becomes important given that certain fluids vital to patient resuscitation (such as blood or blood products) require preservation and storage at low temperatures in order to prevent them from spoiling or contamination. Hence administration of such fluids (e.g. packed red blood cells) requires warming them in order to avoid causing hypothermia in the patient receiving it. Other fluids may require warming prior to being intravenously infused in a patient even though said fluids may be stored at room temperature. It is important to note that the human body's normal temperature, which is critical to normal physiologic homeostasis (typically around 37 degrees Celsius), may be significantly higher than room temperature. Therefore, exposure of patients (intravenous or any other route) to therapeutic fluids that are lower than normal body temperature may not only cause significant discomfort, but also have physiologic consequences which can cause adverse clinical effects and unwanted outcomes. Accordingly, several systems, apparatus, and methods are found in the prior art describing different means to warm fluids such as refrigerated blood and other fluids that require intravenous or intraperitoneal administration. Unfortunately, the prior art solutions are riddled with numerous problems that have yet to be properly addressed.

One common problem is the application of non-uniform electric fields to warm a therapeutic fluid such as intravenous (IV) fluid, which result in an inhomogeneous heating of the liquids. Other problems are presented by conduction heating methods, such as methods that pass blood through heated conduits, which are energy inefficient, less portable and slow, and thus impractical in emergency situations. Other more advanced methods include the introduction of microwave heating, but these methods too have been shown to introduce their own challenges. Primarily, it is now well known that simply heating fluids such as blood (i.e. for example by placing a blood bag inside a conventional microwave oven) carries unacceptable risks given that heating blood in this manner does not result in a uniform distribution of heat throughout the fluid being heated. This important issue is a result of the manner in which microwaves are introduced that leads to generation of hotspots, exposing some areas of the fluid being warmed to excess heat. This will not only be undesirable given the non-uniform nature of heating, but can also lead to adverse effects such as damage to components of the fluid being warmed (i.e. damage to red blood cells or protein structure/function).

While some current methods appear to address hotspots created by systems that implement microwave heating means, these systems appear to rely on components and apparatuses that themselves present additional problems; such problems include introduction of additional steps/equipment (cartridges) in the fluid delivery apparatus (i.e. tubing). This disrupts the continuity of the delivery system (by requiring the tubing to be connected to a cartridge) and creates points where error and contamination can occur, hence raising safety and sterilization concerns. The following examples merely illustrate some of the problems found in the prior art.

One application requiring the warming of such fluids prior to administration includes the warming of peritoneal dialysis dialysate prior to intraperitoneal infusion. For example, certain patients with end-stage renal disease require renal replacement therapy for survival. One modality of renal replacement therapy is peritoneal dialysis (PD); a PD catheter is placed in the patients' abdomen and dialysates (either sterile solutions containing fixed amounts of electrolytes, lactate and dextrose or other infusate such as Icodextrin) are infused into the peritoneal cavity. During treatment, the patient's peritoneal membrane is used as a dialysis membrane and excess serum electrolytes and toxins are removed via diffusion into the dialysate. Given the large volume of dialysates needed each time a patient fills their peritoneal cavity (on average between 2.0-2.5 L), this fluid is usually warmed to between 35° C. and 37° C. to avoid patient discomfort and other unwanted side effects of hypothermia given cool fluid is entering the abdomen. The current system used to warm PD dialysates relies on heat conduction. The warming process is highly inefficient and is fraught with excess time and energy wastage. The system requires warming up a large surface of the dialysis machine and relies on conduction of this heat to a PD dialysate bag, which is placed on top of this surface.

While there are reports of patients/dialysis centers using microwave ovens to warm PD dialysate fluid, this practice is not sanctioned by the US Food and Drug Administration (FDA) or manufacturers of PD solutions, given the potential for formation of hot spots during use of conventional microwave ovens. This is in light of the fact that there are several reported studies in the literature noting mere exposure to RF energy is safe and efficient, and does not lead to disturbance of the PD dialysate content or the integrity of the bag. Several publications provide discussion of these issues such as "Control of microwave heating of peritoneal dialysis solutions" by Deutschendorf A F, Wenk R E, Lustgarten J, Mason P., appearing in Peritoneal dialysis international: journal of the International Society for Peritoneal Dialysis.

1994; 14(2): 163-7; "Microwave ovens for heating fluid bags for continuous ambulatory peritoneal dialysis" by Hudson S, Stewart W K, appearing in British medical journal. 1985; 290(6486):1989; "Rapid warming of infusion solution" by Yamada Y, Yasoshima A. appearing in Surgery, Gynecology & Obstetrics. 1985; 160(5): 400-2; and "Microwave warming of peritoneal dialysis fluid" by Armstrong S, Zalatan S J. appearing in ANNA journal/American Nephrology Nurses' Association. 1992; 19(6): 535-9; discussion 40. However, regardless of these reports, significant safety concerns surrounding hotspot generation and non-uniform warming of dialysate, which can result in serious complications, have precluded routine use of general microwave ovens as a means of warming peritoneal dialysate.

Another important area where warming of therapeutic fluids is of significant value is in critical care when either large volume resuscitation is needed (i.e. liver transplantation, trauma from motor vehicle accidents or battlefield injuries) or in the peri-intra-postoperative period. In many cases the latter scenarios are interrelated and in all cases patients can suffer clinically significant hypothermia. Hypothermia, defined as core temperature <36° C. during a procedure, is a common problem in critical care and among surgical patients. In the case of patients undergoing surgery, an incidence of 4% to 72%, and up to 90% has been reported. Intraoperative hypothermia has been associated with significant clinical complications, including risk of cardiovascular adverse effects, issues with hemostasis and perioperative hemorrhage, increased risk of postoperative infection and disturbed drug metabolism. Given these significant complications, many professional societies, such as the Association of periOperative Registered Nurses (AORN), www.aorn.org, and the National Institute for Health and Care Excellence (NICE), www.nice.nhs.uk, have recommendations in place for preventing and treating during the perioperative period. While there are many factors which may contribute to hypothermia the use of un-warmed fluids for intravenous infusion has been deemed to play a major role. While the positive effects of normothermia in these patients has been documented, the role of warming of patients or infused fluids has been mainly studied using incubators and convection methods. "The effects of warming intravenous fluids on intraoperative hypothermia and postoperative shivering during prolonged abdominal surgery" by Camus Y, Delva E, Cohen S, Lienhart A published in Acta Anaesthesiol Scand. 1996 August; 40(7):779-82. "The effects of intravenous fluids temperature on perioperative hemodynamic situation, post-operative shivering, and recovery in orthopaedic surgery" by Hasankhani H, Mohammadi E, Moazzami F, Mokhtari M, Naghgizadh M M. published in the journal Can Oper Room Nurs J. 2007 March; 25(1):20-4, 26-7. Again, these methods are fraught with inefficiency, lack of portability and excess time requirement. Therefore, novel fluid warming technologies which can address hypothermia in the scenarios mentioned will be of significant value. The application of microwave technology has been limited and will be discussed in the next section.

Another important application involves the need for warming of blood and blood products (red blood cell transfusion); a treatment which becomes necessary to maintain the oxygen-carrying capacity in patients with severe anemia, especially those who have suffered major trauma or patients undergoing major surgery. During resuscitation of the latter patients, multiple units of blood products or packed red blood cells (PRBCs) may be administered in a short period of time. Such products or PRBC units are normally refrigerated at low temperatures of 4±2° C. prior to transfusion. The FDA regulation recommends storage temperature in the range of 1° C.-6° C.; "Safe storage" would be considered to be void if the temperature exceeds 8° C. (See for example FDA "Guide to inspections of blood banks," published by the FDA, Office of Regulatory Affairs Washington. 14 Sep. 1994).

For patients requiring large volumes of blood transfusion, to prevent hypothermia, the PRBCs units must be warmed up rapidly and almost immediately before transfusion. Aside from the inherent energy inefficiency of convection heating methods, using known means that implement conduction, could prove problematic; especially in emergency situations where considerable transfusions are required to be infused rapidly.

Although delays resulting from heating means relying on conduction of heat appeared to have been addressed by microwave heating methods, these systems proved similarly problematic. The use of conventional microwave ovens or other adapted derivatives to warm blood and IV products became popular soon after the introduction of commercial microwave ovens in the mid-1950s and was regularly used up until the 1970s. Such devices offer shorter heating times than the conventional heaters such as those using a water bath, but several reports of complications from overheating of blood products led to abandonment of microwave oven blood warmers. See for example "Danger of overwarming blood by microwave" by Arens J F, Leonard G L published in Jama. 1971; 218(7): 1045-6. Considerable ongoing debates remain regarding the use of these devices (see for example, "Indicators of erythrocyte damage after microwave warming of packed red blood cells" by Hirsch J, Menzebach A, Welters I D, Dietrich G V, Katz N, Hempelmann G. published in Clinical chemistry. 2003; 49(5): 792-9; and "Temperature course and distribution during plasma heating with a microwave device" by Hirsch J, Bach R, Menzebach A, Welters I D, Dietrich G V, Hempelmann G. published in Anesthesia 2003; 58(5): 444-7).

There are several reports that describe the use of various microwave-based techniques to warm blood products, which do not involve heating up a blood bag inside a microwave oven, per se. However, each of these methods is complicated by an apparent inability to avoid hot spots, or use techniques that require the use of a disposable cartridge. The former having the potential to damage or inadequately heat up the fluids; the latter introducing a point of disruption in the delivery of the infusate which can create the potential for clinically significant adverse events such as entry of air, contaminants or infection given that the need for a cartridge breaks the continuous sterile transfusion system (i.e. the tubing connecting the infusate to the patient). In addition, the need for a cartridge adds another layer of cost and complexity which is less desirable. (See for example, "Microwave applications in clinical medicine" by Lantis J C, 2nd, Carr K L, Grabowy R, Connolly R J, Schwaitzberg S D. published in Surgical endoscopy. 1998; 12(2): 170-6; "The limits of bloodwarming: maximally heating blood with an inline microwave blood warmer" by Herron D M, Grabowy R, Connolly R, Schwaitzberg S D. published in The Journal of trauma, 1997; 43(2): 219-26; discussion 26-8; "In-line microwave blood warming of in-date human packed red blood cells" by Pappas C G, Paddock H, Goyette P, Grabowy R, Connolly R J, Schwaitzberg S D. published in Critical care medicine, 1995; 23(7): 1243-50; "The effect of in-line microwave energy on blood: a potential modality for blood warming" by Holzman S, Connolly R J, Schwaitzberg S D. published in The Journal of trauma. 1992;

33(1):89-93; discussion –4; and "Rapid in-line blood warming using microwave energy: preliminary studies." By Schwaitzberg S D, Allen M J, Connolly R J, Grabowy R S, Carr K L, Cleveland R J. published in Journal of investigative surgery: the official journal of the Academy of Surgical Research. 1991; 4(4):505-10).

Accordingly, there is an unanticipated and significant clinical need, which is inadequately addressed at this time for warming fluids. More specifically, there is a need in the art for a fluid warming technique whereby fluids, such as intravenous (IV) fluids, can be warmed to the desired temperature via a warmer apparatus that avoids the potential complications of localized overheating, or exposure to hotspots altogether. Furthermore, there is a need for a fluid warming technique and apparatus that is more portable and does away with cartridges or components that break a closed sterilized system, minimizing risk of error or infection and avoiding safety and sterilization challenges presented by current means.

Therefore, there is a need in the art for a radio frequency fluid warmer and method that may be utilized to warm fluids, including IV fluids, which adequately addresses the problems with the prior art. It is to these ends that the present invention has been developed.

BRIEF SUMMARY OF THE INVENTION

To minimize the limitations in the prior art, and to minimize other limitations that will be apparent upon reading and understanding the present specification, the present invention describes a radio frequency fluid warmer and method that may be utilized to warm therapeutic fluids.

A radio frequency fluid warmer apparatus, in accordance with an exemplary embodiment of the present invention, comprises: a waveguide including first and second electromagnetic ports, an inlet for receiving a fluid, and an outlet for dispensing the fluid; a tube for routing the fluid inside the waveguide between the inlet and the outlet during operation of the apparatus; a source of electromagnetic energy coupled to the first electromagnetic port; and a termination coupled to the second electromagnetic port for preserving a matched waveguide condition.

A radio frequency fluid warmer apparatus, in accordance with another exemplary embodiment of the present invention, comprises: a waveguide including first and second electromagnetic ports, an inlet, and an outlet for receiving a fluid tube that traverses the waveguide; a pathway situated inside the waveguide for routing the fluid tube between the inlet and the outlet; a radio frequency generator coupled to the first electromagnetic port; and a termination coupled to the second electromagnetic port for preserving a matched waveguide condition.

A system for warming intravenous fluids using radio frequency signals, in accordance with an exemplary embodiment of the present invention, comprises: a rectangular waveguide including first and second electromagnetic ports, an inlet situated substantially at a sidewall of the rectangular waveguide for receiving a fluid, and an outlet for dispensing the fluid; a control module configured to: generate radio frequency signals from an energy source; and apply the radio frequency signals to the first electromagnetic port; a tube for routing the fluid inside the rectangular waveguide between the inlet and the outlet during operation of the system; and a termination coupled to the second electromagnetic port for preserving a matched waveguide condition.

It is an objective of the present invention to provide an RF frequency fluid warming device that avoids hot-spots.

It is another objective of the present invention to uniformly warm fluids.

It is yet another objective of the present invention to provide a fluid warming device which does not require any additional supplemental equipment (such as a cartridge) and does not disrupt the continuity of the fluid deliver system.

It is yet another objective of the present invention to provide a compact, energy efficient, transportable fluid warming device.

These and other advantages and features of the present invention are described herein with specificity so as to make the present invention understandable to one of ordinary skill in the art.

BRIEF DESCRIPTION OF DRAWINGS

Elements and embodiments in the figures have not necessarily been drawn to scale in order to enhance their clarity and improve understanding of the invention. Furthermore, elements that are known to be common and well understood to those in the industry are not depicted in order to provide a clear view of the various embodiments of the invention.

FIG. 3 illustrates a top cross-sectional view of a rectangular waveguide showing an exemplary pathway in which a fluid tube may be positioned, in accordance with an exemplary embodiment of the present invention.

DETAILED DESCRIPTION OF THE INVENTION

Figure 1:
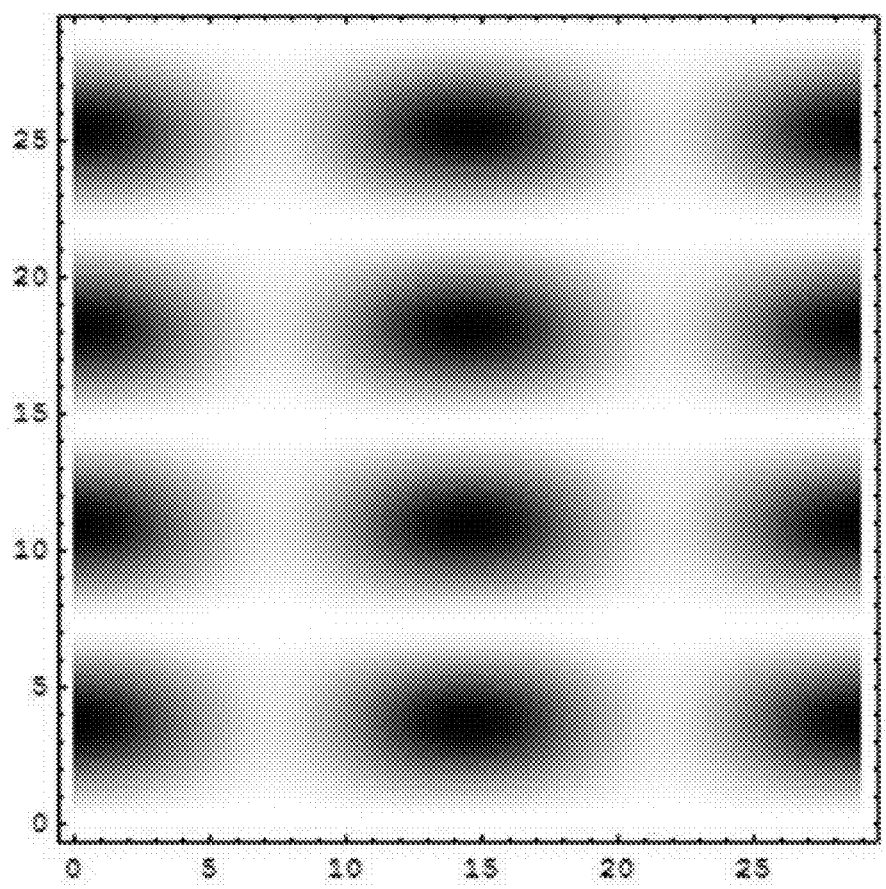
FIG. 1 depicts a formation of hot-spots, which may be found in a typical microwave cavity (such as the inside of a microwave oven), illustrating a common problem of using microwaves to heat certain types of fluids.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

Generally, the present invention involves an in-line real-time radio frequency apparatus for warming fluids, including but not limited to IV fluids. In exemplary embodiments, an in-line heating or warming of fluids may be achieved by means of exposing a fluid having an initial temperature to Radio Frequency (RF) energy. The RF energy may be supplied by an appropriately configured, digitally controlled, RF generator that generates the RF energy into a containment vessel or waveguide. The waveguide typically includes a first terminal end including a point of entry into which a fluid tube may be introduced, and a second terminal end from which the fluid tube may exit the waveguide. Inside the waveguide, a pathway may be formed wherein the fluid tube may rest in a predetermined position. In exemplary embodiments, the pathway guides the positioning of the tube along a transmission-line length of the waveguide, in a manner such that the tube gradually approaches an electromagnetic field inside the waveguide and exits at the second terminal end of the waveguide. The fluid inside the tube, having been gradually exposed to the RF energy inside the waveguide, may absorb energy at a substantially constant rate per unit length, and exit the waveguide at a temperature higher than the fluid's initial temperature. The apparatus is typically non-invasive and may be constructed using a suitable high-frequency transmission-line structure such as a rectangular, circular or elliptical waveguide operating in an appropriate mode of propagation. In exemplary embodiments, the in-line exposure to RF energy is substantially along the transmission-line length, and in a manner, which prevents unsafe over-exposure and overheating of the fluid as it traverses through the warming apparatus, by for example, implementing a gradual and predefined coupling rate of RF energy to the fluid-carrying tube along the transmission-line length. In exemplary embodiments, a non-invasive temperature monitoring subsystem may be employed for monitoring the temperature of the liquid flowing in the tube. Automatic fail-safe controls may comprise of an "operator watch" safety-check to prevent operator errors. Moreover, inlet and outlet temperatures may be continuously sampled to monitor and control the power level of applied RF energy to the waveguide, in order to achieve the desired temperature while avoiding over or under heating.

In the present specification, the term fluid may refer to, but is not limited to, IV fluids, dialysates, blood or blood products, replacement fluids for continuous renal replacement therapy (CRRT), dialysis water, or any other fluid or therapeutic fluid that may be administered to a patient. For example, and without limiting the scope of the present invention, fluids in this disclosure may refer to various concentrations of saline, lactated ringer, D5W, blood products (including but not limited to packed red blood cells, fresh frozen plasma, platelets and cryoprecipitate), peritoneal dialysis dialysate, hemodialysis dialysate/water, continuous renal replacement therapy replacement fluid and dialysates, plasmapheresis and plasma exchange blood products prior to use in patients, or any other fluids including fluids that may require warming prior to or concurrent with medical procedures. Of course, a person of ordinary skill in the art will appreciate that other fluids, including fluids that may not necessarily have therapeutic properties, may be warmed or heated using an apparatus in accordance with the present invention.

An apparatus in accordance with present invention is entirely different from the methodologies previously disclosed in the prior art and avoids the shortcomings of the previous systems. To illustrate the problems addressed by a system in accordance with the present invention, a brief detailed examination of microwave technology explains the causes for concerns with application of devices or any adapted derivatives that employ RF energy as a means to warm fluids, particularly IV fluids. To such ends, and now turning the first figure, FIG. 1 depicts a formation of hot-spots, which may be found in a typical microwave cavity (such as the inside of a microwave oven), illustrating a common problem of using microwaves to heat certain types of fluids.

More specifically, FIG. 1 shows the energy distribution in a microwave cavity or resonator is not uniform, and the temperature of the target (for example a fluid-containing bag) at hotspots (i.e. the dark spots) can easily exceed safe limits. Based on the below analysis, the application of any cavity-based microwave ovens regardless of configuration should be considered as potentially unsafe. This analogy can be extended to any enclosed cavity system that may be used to warm or heat certain fluids, including IV fluids.

A microwave oven in its simplest form comprises of a continuous wave (CW) or pulsed RF source at the 2.45 GHz range. In microwave ovens, the RF source is normally a magnetron which is a high-power high-frequency tube oscillator. Recently, solid state sources are becoming available for such applications. The RF generator is coupled to the microwave cavity or warming cavity. A short section of metallic waveguide connects the RF generator to the warming cavity. The applied RF energy excites a cavity mode in the warming cavity. The formation of a cavity mode is due to propagation of electromagnetic waves between the walls of the enclosed cavity leading to the formation of a standing wave pattern with peaks (nodes) and troughs (antinode), wherein the nodes are hot-spots such as those seen in FIG. 1.

The following explains the causes of hot spot formation inside a microwave cavity. The RF electric field component inside the cavity may be given as follows:

$$E_x = E_1 \cos(k_x x)\sin(k_y y)\sin(k_z z)e^{i\omega t}, \quad (1);$$

$$E_y = E_2 \sin(k_x x)\cos(k_y y)\sin(k_z z)e^{i\omega t}, \quad (2); \text{ and}$$

$$E_z = E_3 \sin(k_x x)\sin(k_y y)\cos(k_z z)e^{i\omega t}, \quad (3),$$

where $\omega$ is the angular frequency of the microwave, and $k_x$, $k_y$ and $k_z$ are given by:

$$k_x = \frac{m\pi}{L_x}, k_y = \frac{n\pi}{L_y}, k_z = \frac{p\pi}{L_z} \text{ and } m, n, p = 0, 1, 2, \ldots, \quad (4),$$

where $L_x$, $L_y$ and $L_z$ are dimensions of the cooking cavity, and $E_1$, $E_2$ and $E_3$ are constrained by:

$$k_x E_1 + k_y E_2 + k_z E_3 = 0, \quad (5)$$

and the average power density absorbed by a load in the microwave (e.g. food) may be given as:

$$<P> \propto <E^2>, \quad (6),$$

where $<E^2> = \frac{1}{2}(|E_x|^2 + |E_y|^2 + |E_z|^2), \quad (7).$

Given suitable values of m, n and q which are a function of cavity size, a typical power distribution may be as shown in FIG. 1. Thus, this shows that an RF cavity structure that generates a standing-wave pattern for RF heating inside an enclosed warming cavity will have hot-spots. Standing-waves are generated when the energy travels in two opposing directions, which occurs when the RF energy is bounced back and forth by reflective (metallic) cavity walls. Therefore, to achieve uniform heating inside a waveguide, the formation of standing waves must be avoided.

Accordingly, the present invention provides for uniform RF heating by implementing a system that instead generates a travelling wave when applying RF energy to the system's waveguide. As will be discussed in turn with reference to the remaining figures, by facilitating the formation of a travelling wave heating structure including a waveguide that is appropriately matched at its terminals, the present invention enables an efficient, quick heating means of warming fluids in a uniform and homologous manner.

Figure 2A:
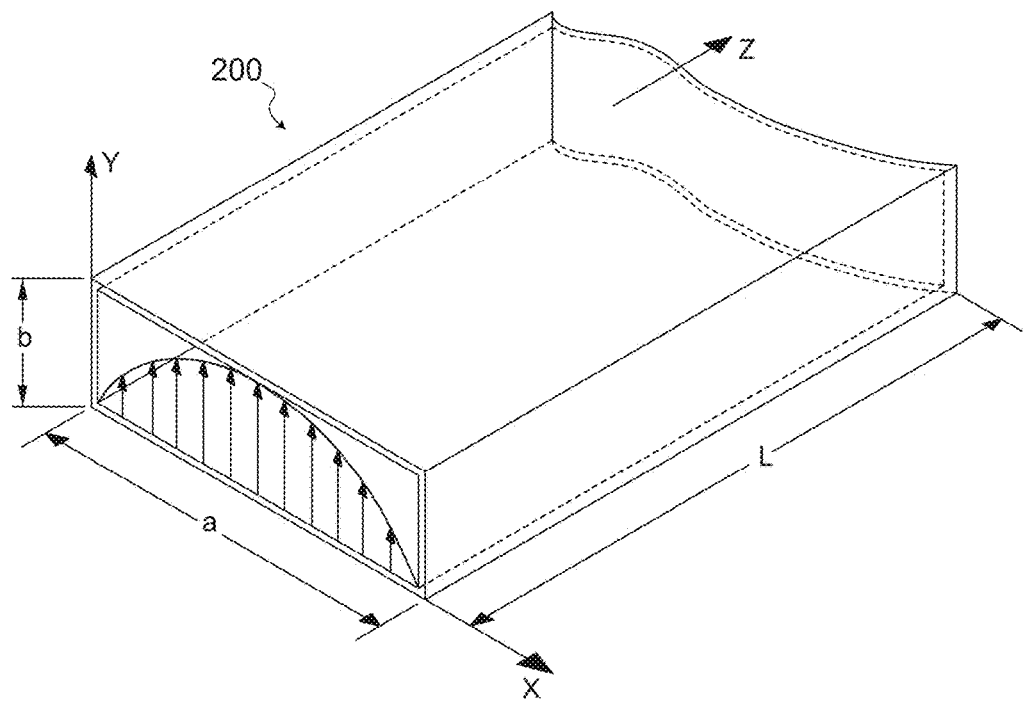
FIG. 2(a) and FIG. 2(b) illustrate an exemplary rectangular waveguide field pattern in accordance with practice of the present invention.
Figure 2B:
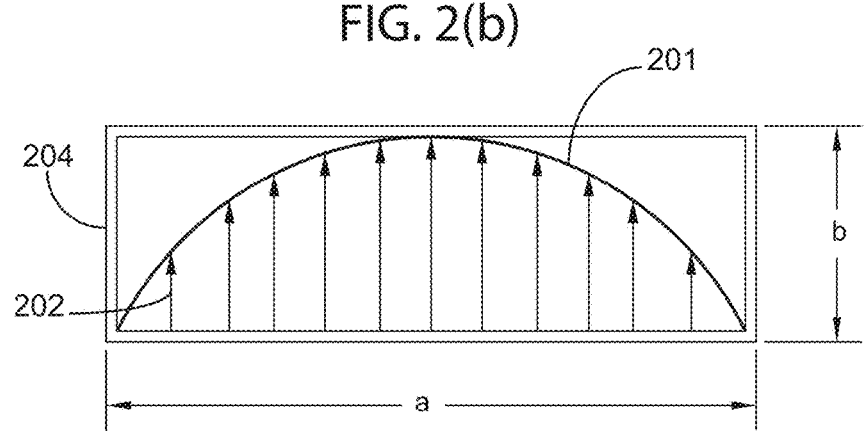

Turning now to the figures depicting the invention, FIG. 2(a) and FIG. 2(b) illustrate an exemplary rectangular waveguide field pattern in accordance with practice of the present invention. More specifically, FIG. 2(a) and FIG. 2(b) illustrate a diagram that helps explain the coupling of energy from a waveguide 200 to a fluid-carrying tube (not shown in this figure), utilizing a specific property of electric field pattern generated inside waveguide 200.

As mentioned above, waveguide 200 in accordance with an exemplary embodiment of the present invention may include any number of structural designs, and may comprise of a rectangular waveguide as shown having a length L, a width a, and a height b; however, this particular geometry is not a limiting case and other geometries with similar field patterns are equally appropriate, including circular or elliptical cross-sections, and variations such as ridged waveguides and others would not deviate from the scope of the present invention.

Waveguide 200 is shown as a substantially rectangular structure, in accordance with an exemplary embodiment of the present invention, having an electric field generated perpendicular (along height b) to the direction of propagation (along length L) through waveguide 200; as shown, the dominant transverse electric (TE) mode waveguide 200 is in $TE_{10}$. In this mode of excitation, the peak of envelope 201 of electric field 202 is half sine in shape, i.e. the field intensity is maximum at the center of waveguide 200's broad dimension (width a) and its intensity decreases to zero approaching each of the waveguide side walls 204. Accordingly, in order to tap the maximum energy from waveguide 200, a fluid-carrying tube may be placed at the center of waveguide 200, meaning positioning the tube at substantially half a and along length L of waveguide 200. Conversely, to minimize the energy absorption of a fluid introduced into waveguide 200, a fluid-carrying tube may be placed closer to the side walls 204. Consequently, as shown in FIG. 2(a) and FIG. 2(b), the location of the fluid-carrying tube (e.g. an IV tube) in waveguide 200 will determine the amount of energy absorption by the fluid-carrying tube.

It should be noted that while the current disclosure focuses on a rectangular waveguide propagation in $TE_{10}$ mode of operation, other geometries and supporting modes may be utilized without deviating from the scope of the present invention.

For example, the envelope of the field intensity across the cross section of a rectangular waveguide can be calculated analytically or simulated using numerical techniques. Such techniques are well known to those skilled in the art. As depicted by the plot of electric field pattern illustrated in FIG. 2, the electric field envelop peaks across the waveguide's cross section; showing a half sinusoidal variation across the broad dimension of waveguide 200. If a waveguide is excited at its $TE_{20}$ mode, a similar analysis will show a full sinusoidal variation and the electric filed will peak twice across the waveguide opening. Accordingly, both $TE_{10}$ and $TE_{20}$ can be utilized for the intended application. As an example, however, and in no way intended to limit the scope of the present disclosure, this specification focuses on the $TE_{10}$ mode as an illustrative embodiment.

As such, in an exemplary embodiment of the present invention, the available RF energy peaks at the center of the broad dimension or width a (as shown in FIGS. 2(a) and 2(b)) and the intensity reduces near the sidewalls. Therefore, if a fluid carrying tube is placed along the length L of waveguide 200 (i.e. within a pathway, for example), the RF energy will interact with the fluid in the tube and the energy absorption rate will be a function of location of the tube within the waveguide's cross-section, so that, with reference to FIGS. 2(a) and 2(b) for example, the absorbed energy is a function of x (or a width along the length of the waveguide). The following figure illustrates such embodiment.

Turning now to the next figure, FIG. 3 illustrates a top view of a rectangular waveguide showing an exemplary cavity, conduit, or pathway in which a fluid tube may be positioned, in accordance with an exemplary embodiment of the present invention. More specifically, waveguide 300 is shown comprising a housing or clam shell, which includes a first shell 301 and a second shell 302, that may be decoupled from each other so that one of the shells acts as a top shell that encloses or envelops portions of a base shell.

In exemplary embodiments, as will be discussed further below with reference to other figures, the top shell is substantially hollow and the base shell (for example, second shell 302) may be filled with a foam structure 302a that is lightweight but allows for the formation of a cavity, conduit or pathway 303 in which to position a fluid tube, such as an IV fluid tube. In the embodiment shown, depicted in a cross-sectional top view, it can be appreciated that the insertion of a tube positioned within pathway 303, which runs along the length or the z-axes of waveguide 300, will alter the hallow waveguide structure in terms of RF energy conduction. As mentioned above, the location of a fluid-carrying tube along pathway 303 will determine the amount of energy absorption or heat generated in the fluid-carrying tube.

In exemplary embodiments, waveguide 300 is a partial dielectric-filled waveguide. As a person of ordinary skill in the art will appreciate, power loss (and conversion to heat) in a waveguide transmission-line is caused by imperfection of wall conductors and the dielectric filling the waveguide. Therefore, input RF power may be gradually attenuated as the input RF signal travels along the guide between RF input port 307 and terminated port 308. The attenuation factor for a transmission-line in may be defined as:

$$\alpha = \frac{\text{Power lost in unit length}}{2 \times \text{power transmitted}}, \quad (8)$$

where: $\alpha = \alpha_c + \alpha_d$; $\alpha_c$=the attenuation factor due to the walls' ohmic resistance; and $\alpha_d$=the dielectric loss per unit length.

Figure 9:
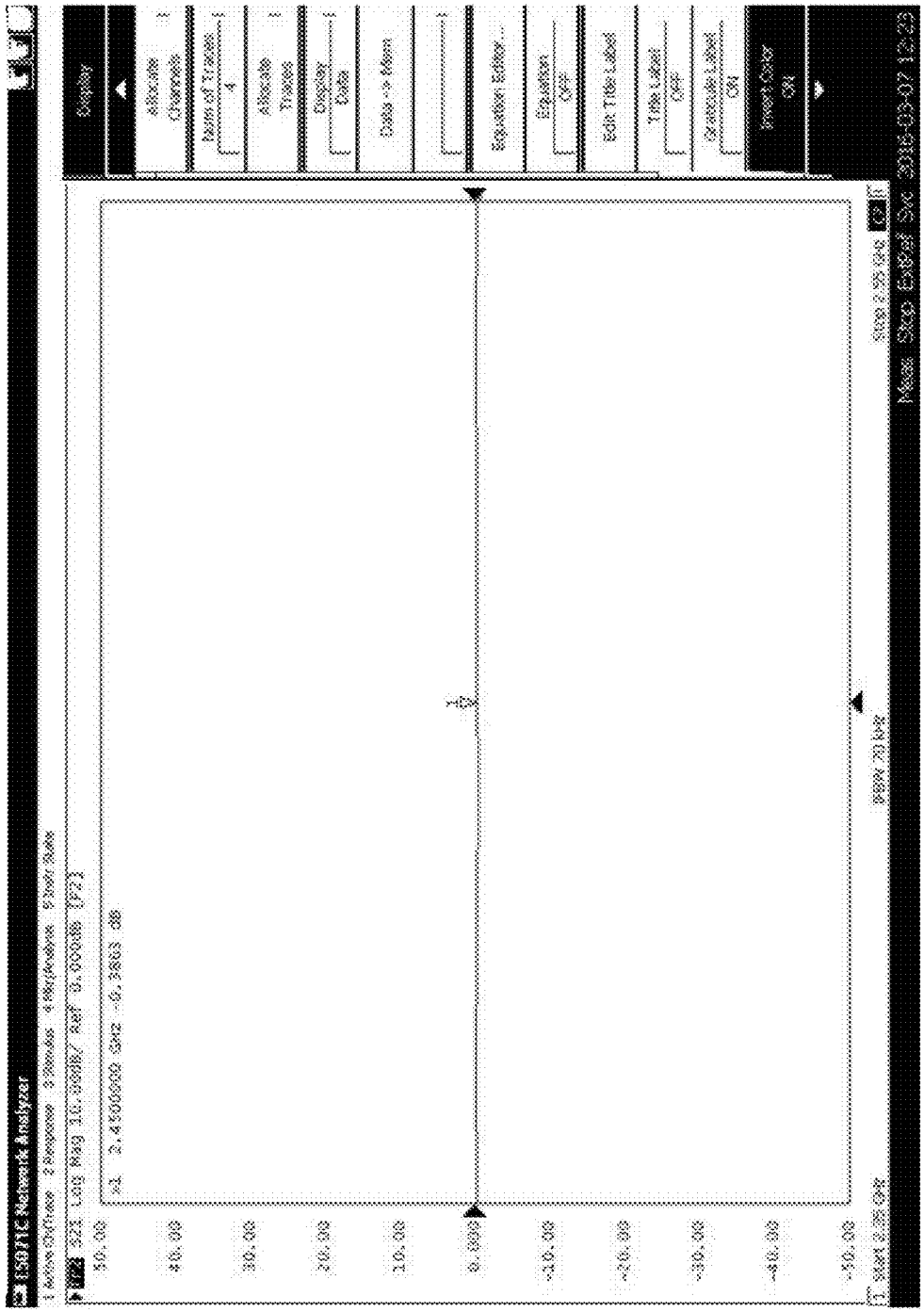
FIG. 9 illustrates a screen-shot of an analysis tool showing infusion tube losses, without liquid.
Figure 10:
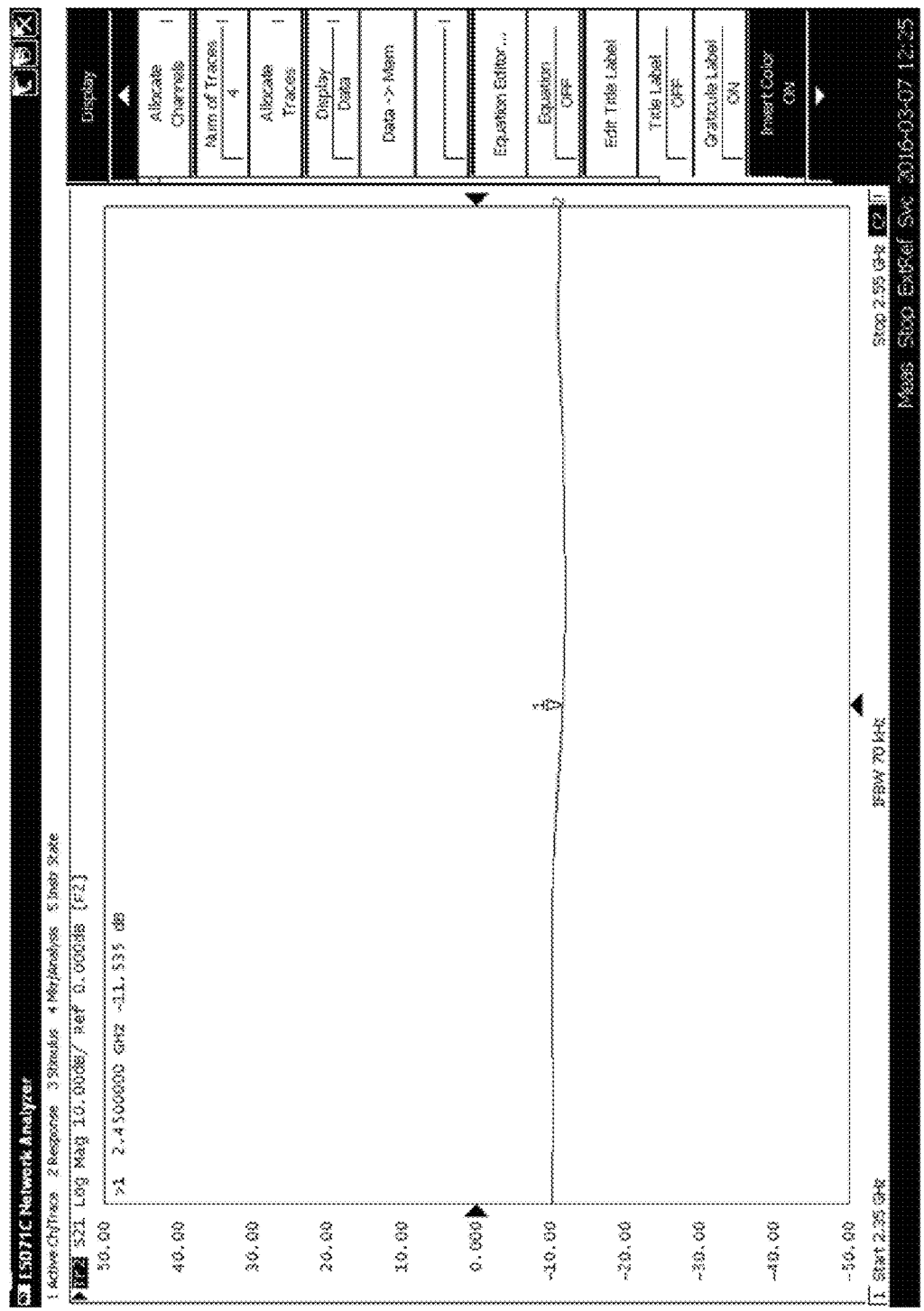
FIG. 10 illustrates a screen-shot of an analysis tool showing infusion tube losses, with liquid.

In an air-filled waveguide (i.e. without a tube inserted), the $\alpha_c \gg \alpha_d$. However, when the fluid-carrying tube is inserted in the waveguide, the waveguide gets loaded and the dielectric loss will dominate, i.e., $\alpha_c \ll \alpha_d$ in which case the fluid (i.e. inside the fluid-carrying tube) absorbs the RF energy and heats up. This is shown in FIG. 9-FIG. 10.

The signal attenuation caused by fluid absorption may be calculated from:

$$\text{insertion loss} = 10 \log e^{2\alpha l} \quad (9),$$

where $\alpha$ is the combined loss-coefficients and is dominated by $\alpha_d$. The $\alpha_d$ is the attenuation factor of loss caused by the tube and the fluid. FIG. 9 shows that the tube loss (with no fluid) is negligibly small whereas the flow of fluid in the tube constitutes the dominant share of loss ($\alpha_d$) as shown in FIG. 10, which is caused by absorption of RF energy and heating the fluid in the tube.

Accordingly, it is noted that the insertion loss of a fluid-carrying tube, or a loaded waveguide, is proportional to the length l where the fluid-carrying tube interacts with the electric field in the waveguide. As discussed earlier, the RF heating would be maximum if the tube is always located at the center of the guide, and the heating rate (i.e. heat generated per unit length) will be highest closer to the RF source or RF input port 307, and lowest closer to the terminated port 308, which is situated at a low intensity RF section of waveguide 300.

However, a fluid warming apparatus in accordance with the present invention preferably, especially for applications involving certain medical fluids, includes a pathway positioned such as pathway 303, which gradually veers away from side-walls 304 towards a center portion of waveguide 300.

In such embodiment, for $TE_{10}$ mode, the attenuation factor $\alpha_d$ will be modified by $$\sin^2 = \left(\frac{m\pi x}{a}\right)$$

term (where for $Th_{10}$, m=1 and n=0). Here "x" (see FIG. 2, FIG. 3) is the variable that defines the tube location across length L of the waveguide. For example, for x=0 at (waveguide wall, or for example waveguide inlet opening 306) the dielectric attenuation (attenuation factor $\alpha_d$) is reduced to zero and no heat is generated assuming dominant $\alpha_d$ as discussed above. The attenuation (absorption) will be maximum at x=a/2 (i.e., at the center of the front wall of the waveguide that includes the inlet).

The following Table 1.0 discloses an exemplary means for a uniform distribution of heat along the length of waveguide 300. Of course, this is shown by way of example and in no way is Table 1.0 intended to limit the scope of the present invention. Assuming a typical waveguide construction for waveguide 300, wherein a fluid-carrying tube has been positioned along pathway 303, and wherein L is 20 cm, the absorption rate in each increment of Δl=1 cm may exemplarily follow the Table 1.0 below, in order to achieve a uniform heat generation.

TABLE 1.0

| Tube length increments | Input power level at each increment | Power absorbed in each increment | Power absorbed dB |
|---|---|---|---|
| 1 | 100 | 0.05 | −13.01029996 |
| 2 | 95 | 0.052631579 | −12.78753601 |
| 3 | 90 | 0.055555556 | −12.55272505 |
| 4 | 85 | 0.058823529 | −12.30448921 |
| 5 | 80 | 0.0625 | −12.04119983 |
| 6 | 75 | 0.066666667 | −11.76091259 |
| 7 | 70 | 0.071428571 | −11.46128036 |
| 8 | 65 | 0.076923077 | −11.13943352 |
| 9 | 60 | 0.083333333 | −10.79181246 |
| 10 | 55 | 0.090909091 | −10.41392685 |
| 11 | 50 | 0.1 | −10 |
| 12 | 45 | 0.111111111 | −9.542425094 |
| 13 | 40 | 0.125 | −9.03089987 |
| 14 | 35 | 0.142857143 | −8.4509804 |
| 15 | 30 | 0.166666667 | −7.781512504 |
| 16 | 25 | 0.2 | −6.989700043 |
| 17 | 20 | 0.25 | −6.020599913 |
| 18 | 15 | 0.333333333 | −4.771212547 |
| 19 | 10 | 0.5 | −3.010299957 |
| 20 | 5 | 1 | 3.85731E-15 |

Figure 8:
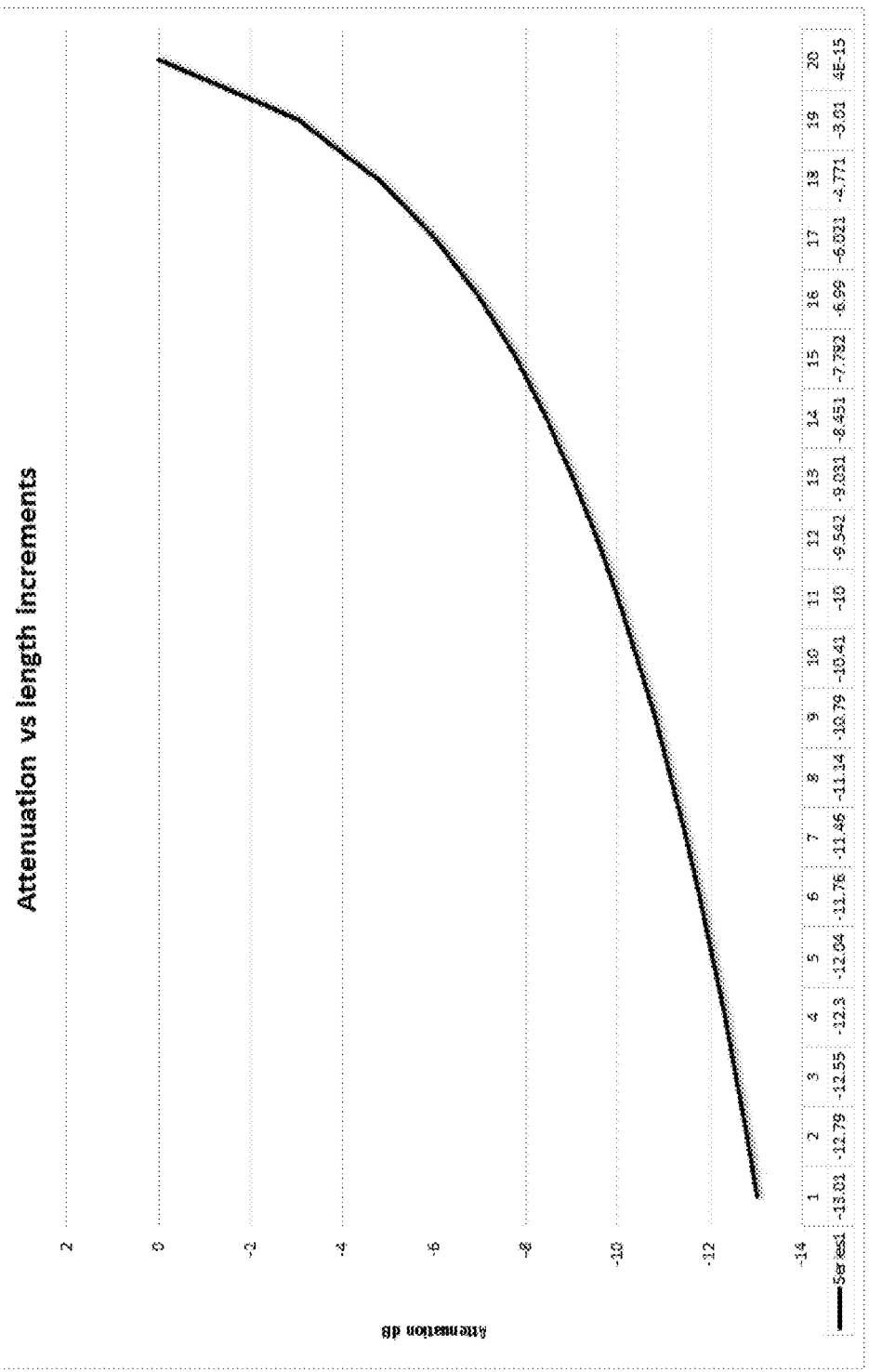
FIG. 8 is a graph showing attenuation versus length increments, which illustrates absorption rate along the length of an intravenous fluid-carrying tube.

More specifically, Table 1.0 above shows the RF energy absorption rate along the length of waveguide for uniform heat generation; this may be plotted as shown in FIG. 8. Referring to equation (7), the RF energy is given as:

$$P \propto \langle E^2 \rangle = \frac{1}{2\mu_{TE}} E_y^2 = \frac{1}{2\mu_{TE}} E_0^2 \sin^2\left(\frac{\pi x}{a}\right), \quad (10)$$

where "a" is the broad dimension of waveguide 300 and "x" is the location of the fluid-carrying tube across the waveguide's length L, and power "P" is constant per unit length along the waveguide length L.

Figure 4:
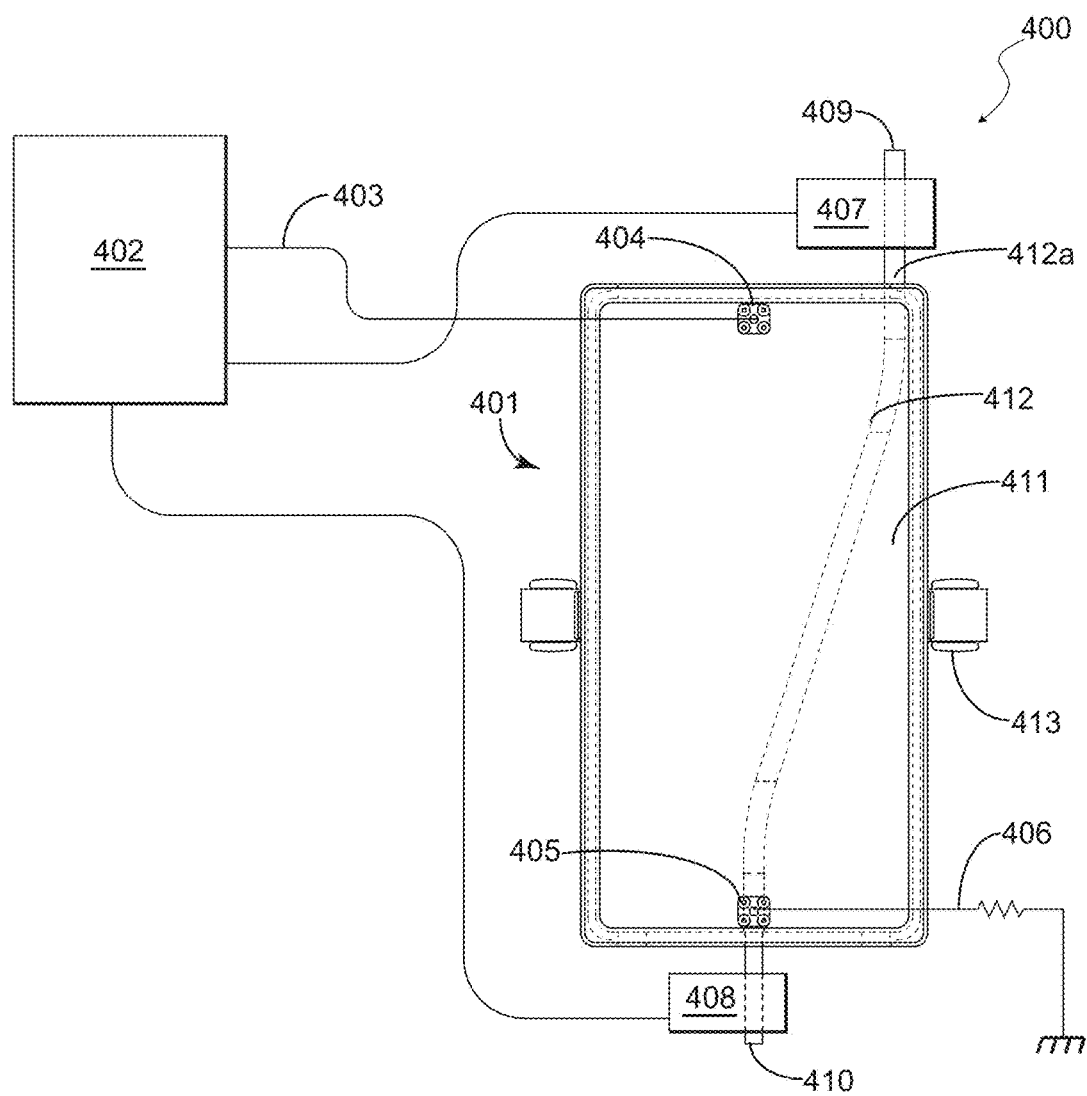
FIG. 4 illustrates a system for warming fluids in accordance with an exemplary embodiment of the present invention.

Turning now to the next figure, FIG. 4 illustrates a system for warming fluids in accordance with an exemplary embodiment of the present invention. More specifically, FIG. 4 depicts an RF fluid warmer system (system 400), which comprises: waveguide 401; an RF source control module (control module 402); an RF input line 403 that introduces RF signals into waveguide 401 via a first electromagnetic port or RF input port 404; a termination comprising terminal port 405 connected to an RF connector 406, which collects any unabsorbed portion of the input power and dumps it in a matched load; and temperature sensors 407 and 408 situated at input terminal end 409 and output terminal end 410, respectively, for non-invasively measuring (and enabling temperature monitoring and control via control module 402) the temperature of the fluid entering and exiting waveguide 401. As in previous figures, waveguide 401 is also shown from a top cross-sectional view in which the interior portion of the containment vessel or waveguide 401 can be appreciated. As shown, waveguide 401 typically includes a structure such as foam structure 411, which includes a pathway 412 (similar to pathway 303 in FIG. 3, for example) that facilitates the positioning, or guides, fluid-carrying tube 412a. Furthermore, waveguide 401 includes two clamps 413 that hold the two halves of the containment vessel or housing of waveguide 401 together after the insertion of the tube and while the apparatus is operational.

The exemplary embodiment depicted in FIG. 4 insures the waveguide (RF transmission line) of system 400 remains properly terminated at all times, albeit with or without fluid running in the tube; the termination eliminating the formation of hotspots inside the waveguide because the termination preserves the matched waveguide condition. As indicated above, RF connector 406 is attached to the surface of waveguide 401 at port 405, which is situated at a terminal end of waveguide 401. The termination, or RF connector 406 that is connected to a monopole radiator inside the waveguide via the second electromagnetic port or termination port 405, is matched to waveguide impedance. The mono pole probe acts as a waveguide-to-coaxial-line transformer. The output of this transformer is connected to a matched load (for example, an RF 50Ω load) capable of absorbing the RF energy flowing in waveguide 401. Such energy could be an excess power not absorbed by infusion fluid or even in the absence of a fluid flow. This component effectively eliminates an otherwise reflection of energy back to control module 402 and prevents the formation of a standing wave pattern (i.e. "hot-spots") within waveguide 401, as discussed above. The matched load is normally attached to the waveguide surface, which will act as a heatsink. In practice, the heat sinking requirement is short lived and is only expected when the RF is "ON" but no fluid is flowing through the tube. Moreover, in exemplary embodiments, in the event that fluid fails to flow in the fluid tube, control module 402 may shut off the RF source after a programable time, in accordance with one or more sets of executable instructions stored or accessible to control module 402.

It is noted here that according to foregoing embodiments of this disclosure, by properly positioning a fluid-carrying tube inside the length (along for example the Z-axis as shown in FIG. 3) of a waveguide, there should be minimal left-over RF energy at the end of the waveguide length, i.e., the tube outlet. Accordingly, the tube outlet can be positioned in the middle section of the waveguide terminal wall (see for example outlet opening 305 depicted in FIG. 3) so that the tube exits from a middle portion of the waveguide. Alternatively, and without limiting the scope of the present invention in any way, a practical alternative may be to position the tube outlet closer to the side-walls so as to eliminate interference with the monopole probe extending into the waveguide from the terminal port. Naturally, other similar alternatives based on design constraints, such as any other convenient location for an outlet opening, may be implemented without deviating from the scope of the present invention. This is more clearly illustrated in a block diagram presented in the following referenced figure.

Figure 7:
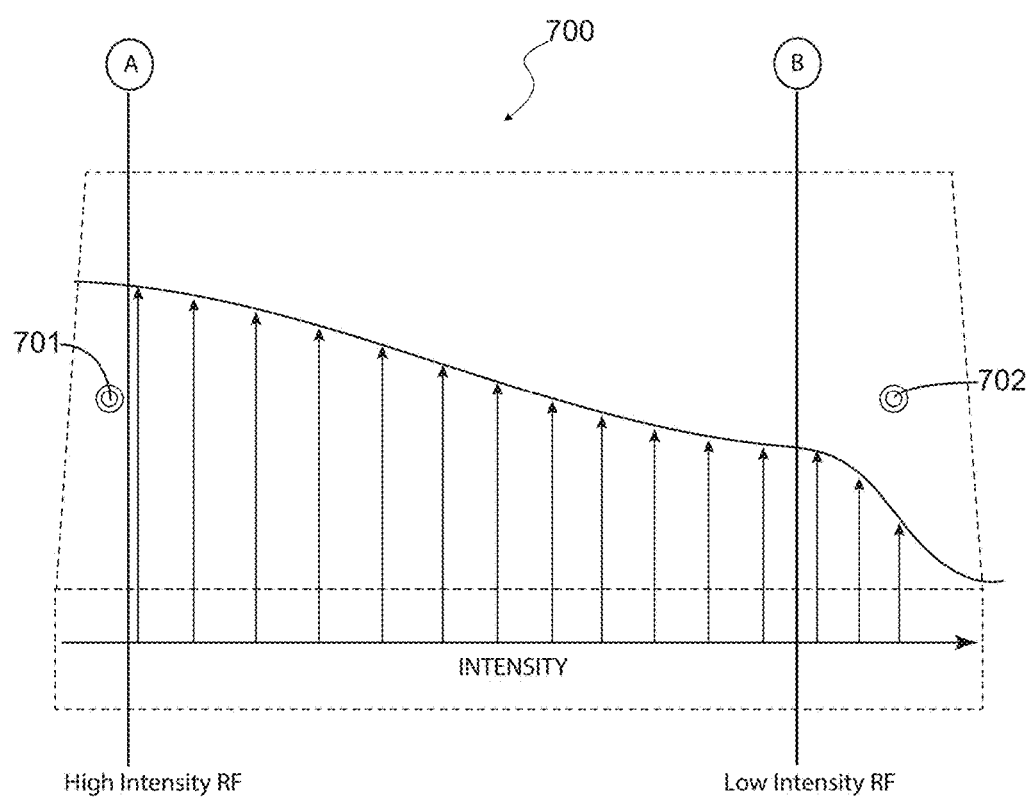
FIG. 7 is a diagram showing an exemplary pathway of a fluid-carrying tube inside a waveguide with corresponding energy intensity therethrough, in accordance with an exemplary embodiment of the present invention.

FIG. 7 is a diagram showing an exemplary pathway of a fluid-carrying tube inside a waveguide with corresponding energy intensity therethrough, in accordance with an exemplary embodiment of the present invention. From this diagram, it may be appreciated that in waveguide 700 including RF input port 701 and RF terminal port 702, the intensity decreases from segment A near the RF input port where RF signals are introduced into waveguide 700, to segment B near RF terminal port 702 where an RF connector collects any unabsorbed portion of the input power and dumps it in a matched load (i.e. termination). As mentioned above, because there may be some structural design considerations that are facilitated by alternative placements of an outlet for a fluid carrying-tube, different positions may be selected for such outlet since as shown in the FIG. 7, after a certain segment B along the length of waveguide 700, the RF intensity is low and will not significantly affect the fluid inside the tube so far as the position out of which the tube exits the waveguide. As mentioned above, however, it can be appreciated from FIG. 7 that an inlet or input portion of a pathway traversing the waveguide is preferably substantially at a sidewall of the waveguide, since the intensity at or near segment A is high and thus could, for example, damage certain fluids.

The above embodiments provide an important and useful advantage of having a terminated waveguide warmer, wherein no priming is required during the startup phase of the fluid warmer. A start-up process in accordance with practice of exemplary embodiments of the present invention may be as follows: Turn on RF generator (the RF termination absorbs the unused RF energy); Turn on the fluid, (where the fluid in the tube will absorb the RF energy and very little will be absorbed by the terminating load); Allow trapped air to exit; and Start the infusion. It is pointed out that this process does not require priming the fluid warmer during which cold fluid has to be collected and disposed.

Figure 5A:
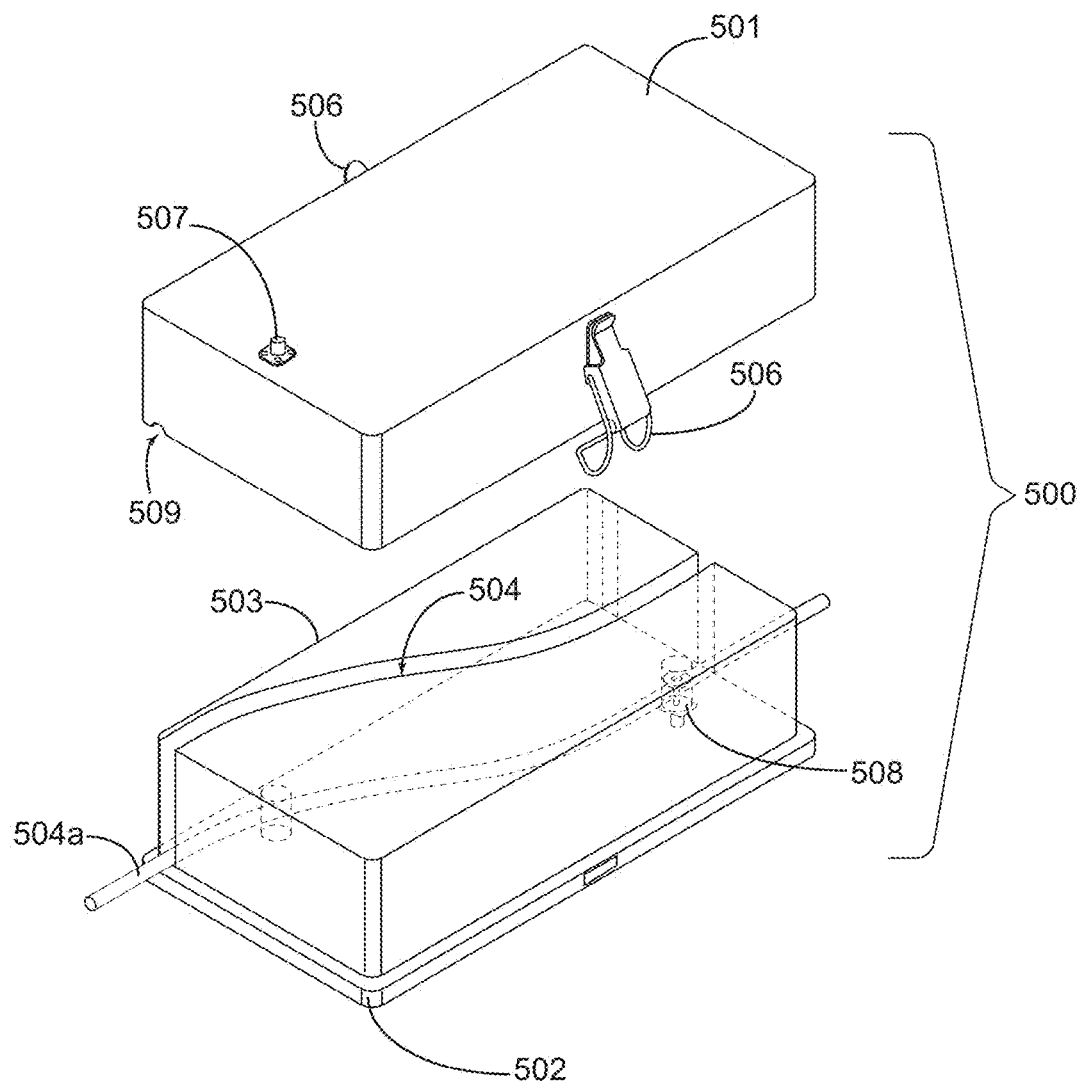
FIG. 5(a) illustrates a fluid warming apparatus for a system for warming fluids in accordance with an exemplary embodiment of the present invention.
Figure 5B:
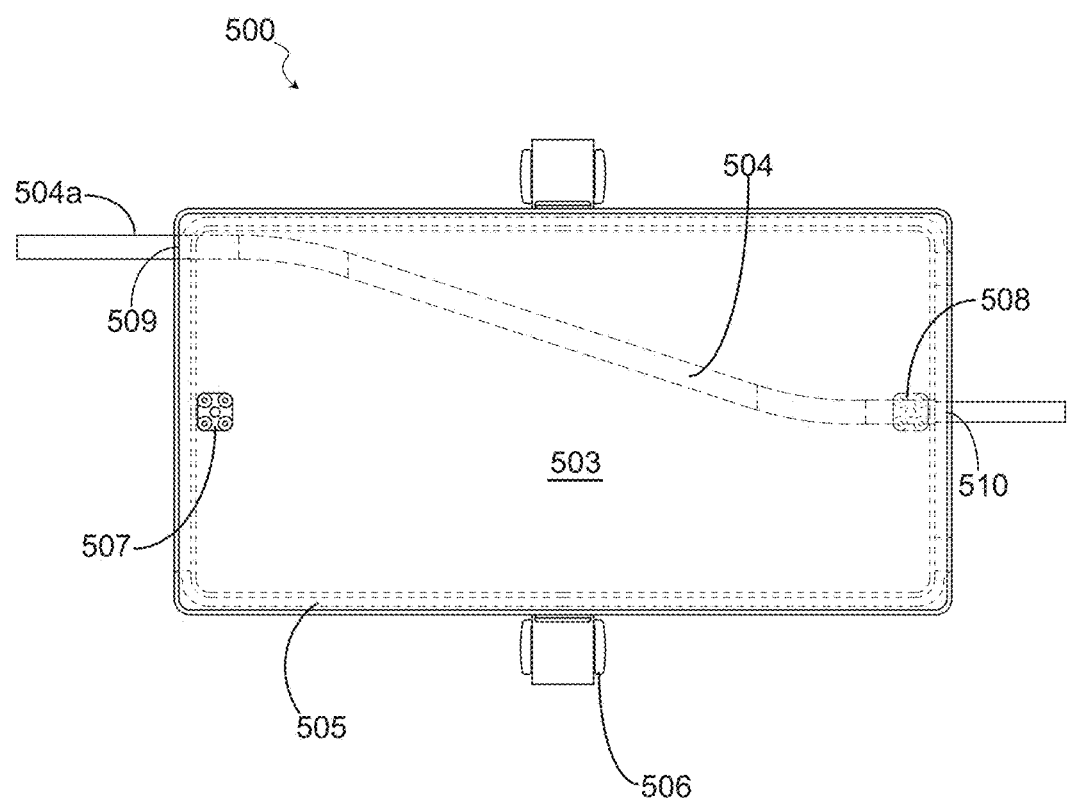
FIG. 5(b) illustrates a cross-sectional top view of the apparatus illustrated in FIG. 5(a).
Figure 6A:
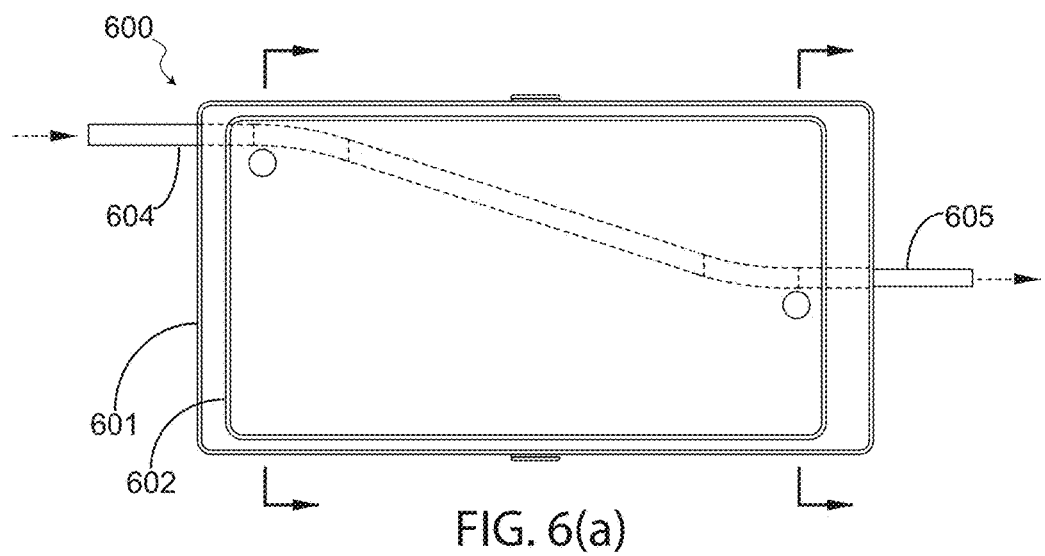
FIG. 6(a) illustrates a top cross-sectional view of a fluid warming system in accordance with an exemplary embodiment of the present invention.
Figure 6B:
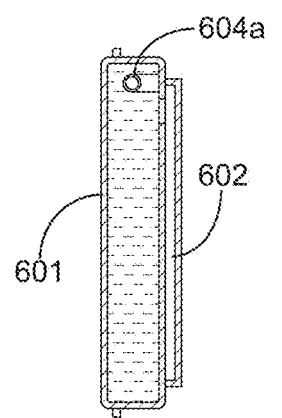
FIG. 6(b) illustrates a front view of the fluid warming system depicted in FIG. 6(a).
Figure 6C:
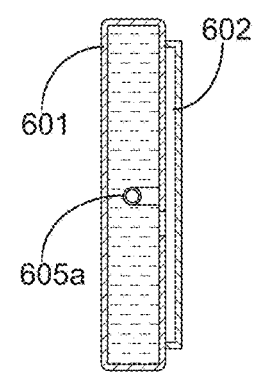
FIG. 6(c) illustrates a rear view of the fluid warming system depicted in FIG. 6(a).
Figure 6D:
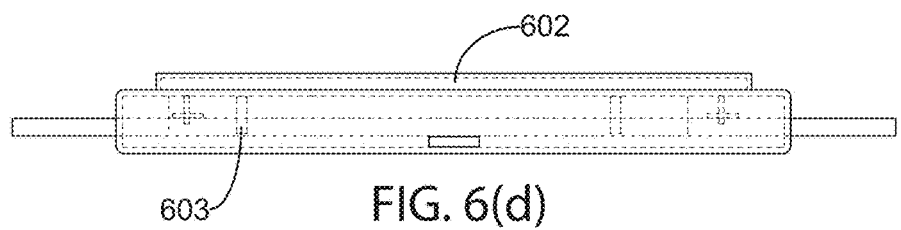
FIG. 6(d) illustrates a side cross-sectional view of the fluid warming system depicted in FIG. 6(a).

Turning now to the next figures, FIG. 5(*a*) illustrates an RF fluid warming apparatus for a system for warming fluids in accordance with an exemplary embodiment of the present invention; and FIG. 5(*b*) illustrates a cross-sectional top view of the apparatus illustrated in FIG. 5(*a*). More specifically, FIGS. 5(*a*) and 5(*b*) depict an RF fluid warming apparatus 500 that may be employed with a system similar to system 400, wherein apparatus 500 comprises: a housing including a first clam cover or shell 501; a base or shell 502, which includes a foam structure 503 comprising a pathway 504; RF choke edges 505; and clamps 506 for securing shells 501 and 502 together when closed.

Because the shells clam together and a fluid tube may be positioned along pathway 504, the present invention does not require disposable cartridges or other add-on components that may disturb a sterilized system. All that is required is any standard tubing (IV tubing, for example) which can be inserted into apparatus 500 with no breakage of the sterile closed tubing system. Of course, other structural designs may be implemented without deviating from the scope of the present invention, but FIG. 5(*a*) and FIG. 5(*b*) depict one exemplary embodiment in which a cover or clam shell 501 can mate or register with a base or shell 502 in order to form the waveguide of apparatus 500. RF chokes may be designed into mating edges 505 of each clam shell to prevent RF leakage.

Foam structure 503 may comprise a low loss foam, which as mentioned above forms a preset profile or pathway 504 for tube 504*a*. In exemplary embodiments, and in no way limiting the scope of the present invention, the foam material of foam structure 503 may be polystyrene or similar polymers. If apparatus 500 is implemented with system similar to system 400, with a separate RF source controller module (for example), input RF connectors 507 may couple the RF energy into the waveguide via a first electromagnetic port and RF connector 508 may collect any unabsorbed portion of the input power, via a second electromagnetic port, and dumps it in a matched load as explained above.

While in operation, clamps 506 for securing shell 501 and shell 502 hold the two halves of the waveguide together after the insertion or positioning of tube 504*a*; insertion or positioning of tube 504*a* may be achieved by opening the two halves and placing tube 504*a* within pathway 504 of foam structure 503 in the predefined position between inlet 509 and outlet 510. In exemplary embodiments, pathway 504 is a fitted pathway, meaning that tube 504*a* fits therein snuggly and securely. A fluid inside fluid-carrying tube 504*a* enters the waveguide at inlet 509 and leaves apparatus 500 via outlet 510. This configuration eliminates the need for a disposable cartridge that has been proposed by prior art. The advantage is twofold: (1) there is no breakage of the closed sterile infusion environment where contamination and infection can be introduced; and (2) cost of disposable cartridges proposed by prior art are entirely eliminated.

Other variations of a housing for apparatus 500 may be possible without deviating from the scope of the present invention. For example, and without limiting the present invention, shell 501 may implement a hinged means, snap on fasteners, screws, or any other fastening means. Importantly, the housing or cover should enclose the waveguide securely and in a manner that prevents leakage.

Turning now to the next set of figures, FIG. 6(*a*) illustrates a top cross-sectional view of a fluid warming system in accordance with an exemplary embodiment of the present invention, which is compact and implements a control module circuitry coupled to a compact housing configured to house a waveguide and the control module circuitry; FIG. 6(*b*) illustrates a front view of the fluid warming system depicted in FIG. 6(*a*); FIG. 6(*c*) illustrates a rear view of the fluid warming system depicted in FIG. 6(*a*); and FIG. 6(*d*) illustrates a side cross-sectional view of the fluid warming system depicted in FIG. 6(*a*). More specifically, these figures depict RF fluid warming system 600, which comprises: an RF fluid warming apparatus including a waveguide housed in a first compartment 601 of a housing with an inlet opening 604*a* and an outlet opening 605*a* for positioning a first end 604 of a fluid-carrying tube through a pathway formed within an internal structure of the waveguide; and an RF source, control module circuitry housed in a second compartment 602 adjacent to the first compartment 601, wherein the RF source and the control module circuitry comprise a printed circuit board(s) including sensors coupled therein.

This exemplary embodiment comprises a compact variation of an RF fluid warming apparatus, which offers several advantages compared to the application of standard waveguides. For example, and without deviating from the scope of the present invention, the aspect ratio of a standard waveguide may typically be 2 to 1 (i.e., in FIG. 2, a=2b). This is required for maximum power handling which could be as high as a megawatt of RF peak power. In an RF fluid warming apparatus in accordance with an exemplary embodiment of the present invention, the average power need not exceed 1 kW. Therefore, it is possible to reduce the waveguide height with no detrimental effect on its performance. Accordingly, the apparatus depicted in FIG. 6(*a*)-(*d*) comprises a reduced height waveguide, which reduces the size and increases the field intensity for stronger coupling to the fluid traveling through the tube.

The structure of the waveguide housed in compartment 601 is similar to that shown and described throughout this disclosure, and may include a foam structure or similar component for positioning the tube in the waveguide. However, the reduced height waveguide will be slimmer and lighter. Moreover, as shown in FIG. 6(*d*), an additional compartment is constructed on a surface to the waveguide so as to allow a printed board, or control board to be securely housed adjacent to the first compartment. The control module housed in compartment 602 typically includes, as mentioned above, the RF source and the controller circuitry. It is noted here that the RF connectors and cables are eliminated and micro-strip traces may be attached to the RF probes 603 exciting the waveguide section.

In an exemplary embodiment, the control module includes a controller configured to: manage overall control of system 600 during operation; execute failsafe operations of self-administered procedures; enable custom remote programing of warmer operating mode; and execute one or more executable instructions concerning patient-specific programing and record keeping. As may be appreciated by a person of ordinary skill in the art, other automated functions, programs and executable instructions may be implemented with system 600 without limiting or deviating from the scope of the present invention. Similarly, as with system 400, temperature sensors may be coupled to or implemented with the control module in order to implement non-invasive temperature monitoring probes at the input opening 604*a* and output opening 605*a* of the unit. As mentioned above, such feedback information may be used by the control module to adjust the output power of the RF generator and therefore, fluid temperature may be precisely controlled.

A typical application of the apparatus discussed here would be warming of peritoneal dialysis dialysate prior to infusion. However, peritoneal dialysis is used here as just one example of how this device can be used as a warmer of biological, pharmaceutical or otherwise medical fluids. Other applications may include administration of blood during warfare or armed combat, in which soldiers require quick transfusions due to sever battle wounds. A system in accordance with the present invention is typically compact and highly portable, which means a waveguide a control module may be compact enough to take on the field by armed forces or medical personnel, carried by first responders in emergency vehicles, or easily transported with a patient—whether at a hospital, clinic or at the patient's home.

An apparatus for warming fluids using radio frequency has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A radio frequency fluid warmer apparatus, comprising:
a first shell;
a waveguide including first and second electromagnetic ports, an inlet for receiving a fluid, and an outlet for dispensing the fluid;
a tube for routing the fluid inside the waveguide between the inlet and the outlet during operation of the apparatus;
a source of electromagnetic energy coupled to the first electromagnetic port;
a termination coupled to the second electromagnetic port for preserving a matched waveguide condition; and
a second shell configured to register with the first shell, wherein the second shell comprises a structure including a pathway for positioning the tube inside the waveguide.

2. The apparatus of claim 1, wherein:
the first electromagnetic port is situated in closer proximity to the inlet than to the outlet of the waveguide; and
the second electromagnetic port is situated in closer proximity to the outlet than to the inlet of the waveguide.

3. The apparatus of claim 1, wherein the waveguide further includes a pathway for positioning the tube inside the waveguide.

4. The apparatus of claim 1, wherein the radio frequency signals are applied along a length of the waveguide.

5. The apparatus of claim 1, wherein the waveguide is a rectangular waveguide and the inlet is situated substantially at a sidewall of the rectangular waveguide.

6. The apparatus of claim 5, wherein a position x of the tube along a width of the rectangular waveguide is given by:

$$P \propto \ <E^2> = \frac{1}{2\mu_{TE}}E_y^2 = \frac{1}{2\mu_{TE}}E_0^2\sin^2\left(\frac{\pi x}{a}\right).$$

7. The apparatus of claim 5, wherein the second electromagnetic port is situated in proximity to the outlet and substantially at the center of a back wall of the waveguide, and wherein a pathway inside the waveguide positions the tube between the inlet and the outlet.

8. The apparatus of claim 1, further comprising:
one or more sensors situated in proximity to the inlet and outlet of the waveguide; and
a control module in communication with the one or more sensors, the control module configured to:
monitor a temperature of the fluid inside the tube based on sensing data of the one or more sensors; and
control a power level of the source of electromagnetic energy in response to the sensing data.

9. The apparatus of claim 1, further comprising an electromagnetic choke implemented into mating edges of the first and second shells to prevent electromagnetic leakage.

10. A radio frequency fluid warmer apparatus, comprising:
a first shell;
a waveguide including first and second electromagnetic ports, an inlet, and an outlet for receiving a fluid tube that traverses the waveguide;
a pathway situated inside the waveguide for routing the fluid tube between the inlet and the outlet;
a radio frequency generator coupled to the first electromagnetic port;
a termination coupled to the second electromagnetic port for preserving a matched waveguide condition; and
a second shell configured to register with the first shell, wherein the second shell comprises a structure that forms the pathway for positioning the tube inside the waveguide.

11. The apparatus of claim 10, wherein the waveguide is a rectangular waveguide and the inlet is situated substantially at a sidewall of the rectangular waveguide.

12. The apparatus of claim 11, wherein a position x of the tube along a width of the rectangular waveguide is given by:

$$P \propto \ <E^2> = \frac{1}{2\mu_{TE}}E_y^2 = \frac{1}{2\mu_{TE}}E_0^2\sin^2\left(\frac{\pi x}{a}\right).$$

13. The apparatus of claim 10, further comprising:
one or more sensors situated in proximity to the inlet and outlet of the waveguide; and
a control module in communication with the radio frequency generator and the one or more sensors, the control module configured to:
monitor a temperature of the fluid inside the tube based on sensing data from the one or more sensors; and
control an output of the radio frequency generator in response to the sensing data.

14. The apparatus of claim 10, wherein the structure that forms the pathway for positioning the tube inside the waveguide comprises a foam structure.

15. A system for warming intravenous fluids using radio frequency signals, comprising:
a rectangular waveguide housed in a first compartment of an enclosure, the rectangular waveguide including first and second electromagnetic ports, an inlet situated substantially at a sidewall of the rectangular waveguide for receiving a fluid, and an outlet for dispensing the fluid;
a control module housed in a second compartment of the enclosure and configured to:
generate radio frequency signals from an energy source; and
apply the radio frequency signals to the first electromagnetic port;
a tube for routing the fluid inside the rectangular waveguide between the inlet and the outlet of the rectangular waveguide during operation of the system; and
a termination coupled to the second electromagnetic port for preserving a matched waveguide condition.

16. The apparatus of claim 15, wherein the rectangular waveguide further includes a pathway for positioning the tube inside the waveguide.

17. The apparatus of claim 15, wherein a position x of the tube along a width of the rectangular waveguide is given by:

$$P \propto \ <E^2> = \frac{1}{2\mu_{TE}}E_y^2 = \frac{1}{2\mu_{TE}}E_0^2\sin^2\left(\frac{\pi x}{a}\right).$$

18. The apparatus of claim 16, wherein the radio frequency signals are applied along a length of the rectangular waveguide.

* * * * *